United States Patent
Nguyen et al.

(10) Patent No.: US 10,954,488 B2
(45) Date of Patent: Mar. 23, 2021

(54) **EXTRACT OF UNDIFFERENTIATED CELLS OF *MIMOSA PUDICA* AND USES THEREOF IN DERMO-COSMETICS**

(71) Applicant: PIERRE FABRE DERMO-COSMETIQUE, Boulogne-Billancourt (FR)

(72) Inventors: Thien Nguyen, Rouffiac-Tolosan (FR); Adrien Cousy, Beaumont sur Leze (FR)

(73) Assignee: PIERRE FABRE DERMO-COSMETIQUE, Boulogne-Billancourt (FR)

(*) Notice: Subject to any disclaimer, the term of this patent is extended or adjusted under 35 U.S.C. 154(b) by 74 days.

(21) Appl. No.: 16/309,750

(22) PCT Filed: Jun. 14, 2017

(86) PCT No.: PCT/EP2017/064640
§ 371 (c)(1),
(2) Date: Dec. 13, 2018

(87) PCT Pub. No.: WO2017/216274
PCT Pub. Date: Dec. 21, 2017

(65) Prior Publication Data
US 2019/0136181 A1    May 9, 2019

(30) Foreign Application Priority Data
Jun. 16, 2016    (FR) ...................... 1655630

(51) Int. Cl.
| | | |
|---|---|---|
| *C12N 5/04* | (2006.01) |
| *A61Q 19/08* | (2006.01) |
| *A61K 31/165* | (2006.01) |
| *A61K 31/198* | (2006.01) |
| *A61K 31/7024* | (2006.01) |
| *A61K 36/48* | (2006.01) |
| *A61K 8/9789* | (2017.01) |
| *A61K 31/4412* | (2006.01) |
| *C12N 5/00* | (2006.01) |
| *A61P 17/18* | (2006.01) |
| *A61P 17/00* | (2006.01) |
| *A61P 29/00* | (2006.01) |
| *A61K 8/42* | (2006.01) |
| *A61K 8/44* | (2006.01) |
| *A61K 8/60* | (2006.01) |
| *B01D 11/02* | (2006.01) |
| *B01D 21/26* | (2006.01) |

(52) U.S. Cl.
CPC .................. *C12N 5/04* (2013.01); *A61K 8/42* (2013.01); *A61K 8/445* (2013.01); *A61K 8/60* (2013.01); *A61K 8/9789* (2017.08); *A61K 31/165* (2013.01); *A61K 31/198* (2013.01); *A61K 31/4412* (2013.01); *A61K 31/7024* (2013.01); *A61K 36/48* (2013.01); *A61P 17/00* (2018.01); *A61P 17/18* (2018.01); *A61P 29/00* (2018.01); *A61Q 19/08* (2013.01); *B01D 11/0288* (2013.01); *C12N 5/0037* (2013.01); *A61K 2236/00* (2013.01); *A61K 2236/11* (2013.01); *A61K 2800/522* (2013.01); *B01D 21/262* (2013.01)

(58) Field of Classification Search
CPC ......... C12N 5/04; C12N 5/0037; C12N 15/82
See application file for complete search history.

(56) References Cited

U.S. PATENT DOCUMENTS 6,290,993 B1 * 9/2001 Anderson ............ A61K 8/9789
424/725

OTHER PUBLICATIONS

Englert ("C-Glycosylflavones from Aerial Parts of Mimosa Pudica", Phytochemical Notes, 60: p. 194, (1993).*
Murashige (Physiologia Plantarium; vol. 15, 1962, 473-497).*

* cited by examiner

*Primary Examiner* — Pancham Bakshi
(74) *Attorney, Agent, or Firm* — Birch, Stewart, Kolasch & Birch, LLP

(57) ABSTRACT

The present invention relates to a preparation obtained from an in vitro culture of undifferentiated cells of *Mimosa pudica*, as well as to the preparation method thereof; a cosmetic or dermatological composition comprising said preparation; and the uses thereof for the treatment of inflammatory skin conditions, as an antioxidant agent in the treatment of oxidative stress caused by environmental pollution, and as an anti-aging agent.

10 Claims, 4 Drawing Sheets

Figure 1:
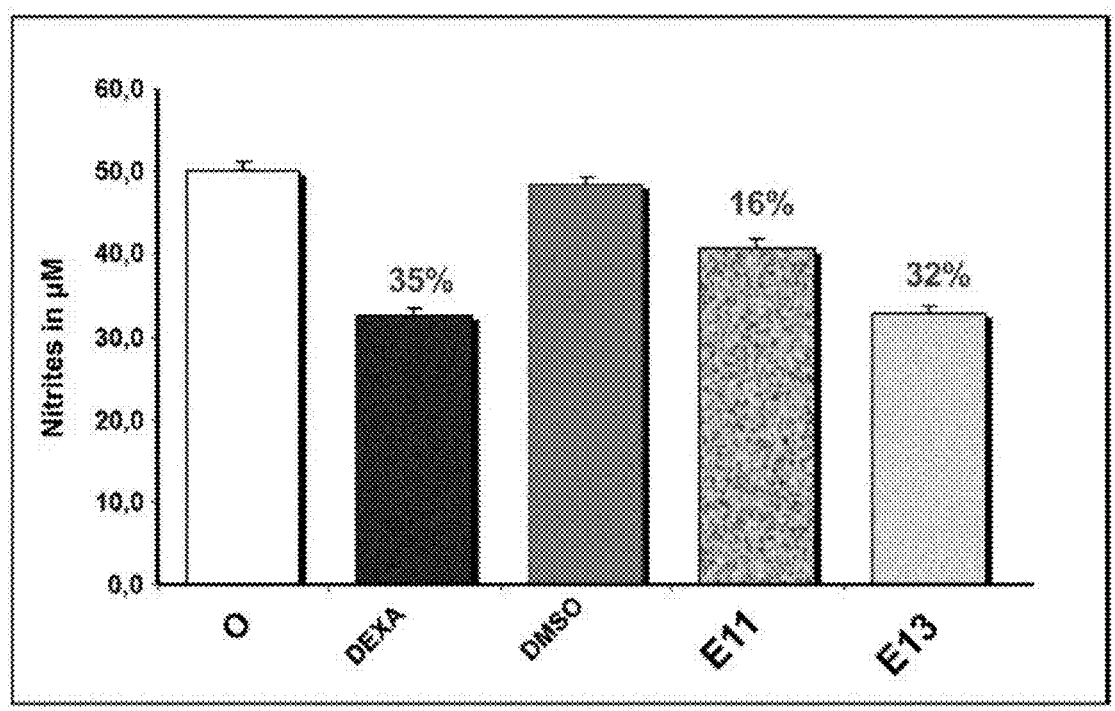

EXTRACT OF UNDIFFERENTIATED CELLS OF *MIMOSA PUDICA* AND USES THEREOF IN DERMO-COSMETICS

The present invention concerns a preparation derived from an in vitro culture of undifferentiated cells of *Mimosa pudica* and the process for preparing same; a cosmetic or dermatological composition comprising said preparation; and uses thereof for the treatment of inflammatory skin disorders, as antioxidant including the treatment of oxidative stress due to environmental pollution, and as anti-ageing agent.

*Mimosa pudica* is a medicinal plant that has for several centuries been used in Asia to treat inflammation. *Mimosa pudica* Linn. (Fabaceae) is known for its antidiabetic (Marles 1995), antidepressant (Molina 1999), anti-inflammatory (Patel 2014), antioxidant (Patro 2016) and antibacterial (Bhakuni 1969) properties. It is also used in wound healing (Paul et al., 2010. Int J Bio Med Res 1(4):223-227).

The methanolic extract of *Mimosa pudica* leaves contains active molecules such as terpenes, flavonoids, glycosides, alkaloids, quinines, phenols, tannins, saponins and coumarins (Gandhiraja et al. 2009). The phenolic molecules contained express strong antioxidant activity (Zhang et al. 2011. Pharmacogn. Mag 4:35-39). However, a major molecule isolated from the plant is highly noted for its toxicity: mimosine. This is a non-protein amino acid (beta-N(3-hydroxy-4-pyridone)-alpha-amino propionic acid). It has been shown to induce adverse effects in animals, such as loss of appetite, hair loss, reproductive disorders (Kulp K. S. 1996. Toxicology and applied pharmacology. 139:356-364). It has also been shown to inhibit seed germination and DNA synthesis in cultured cells (Williams R D et al., 2007. Allelopathy J. 19(2):423-430; Stuenzi et al., 1979). It seems that mimosine is synthesized by the plant in order to defend itself against the ruminants that graze it: it causes digestive problems in animals. The presence of mimosine in extracts of *Mimosa pudica* is a limiting factor for the valorization of this medicinal plant. One approach would consist in finding purification means to remove it, but this approach complicates the processes and requires more stringent monitoring and therefore higher production costs.

There is abundant literature for preparing extracts with polar and non-polar solvents. Document KR 10-1064848 describes extracts from the plant, using organic solvents such as ethanol and ethyl acetate, for the treatment of autoimmune diseases.

In the context of the present invention, the Applicant has demonstrated a novel valorization of *Mimosa pudica* via an alternative route: the in vitro culture of undifferentiated, totipotent cells. Indeed, it was surprisingly noticed that bioreactor culture of these cells makes it possible to obtain a preparation significantly depleted in mimosine; said preparation having very attractive properties for the treatment of inflammatory skin disorders, oxidative stress, and skin ageing. These properties were more particularly surprising when a bioconversion step is carried out during the process, this step producing novel metabolites that potentiate the antioxidant activity more particularly. Unexpectedly, the Applicant observed that these metabolites are part of the N-phenylpropenoyl-L amino acids (NPAs). NPAs as such are known and highly sought after for their advantageous pharmacological activity (Hensel et al. Planta Med. 2007; 73:142-150; Zeng et al. J. Agric. Food Chem. 2011; 59:5342-5350). Heretofore, it has not been known that the *Mimosa pudica* plant contains antioxidants such as NPAs.

In inflammatory dermatoses, in skin lesions in patients with atopic dermatitis of the epidermis, there is overexpression of the cytokine TSLP (thymic stromal lymphopoietin), which plays a crucial role in the pathogenesis of allergic diseases mediated by a Th2-type cellular response (Takai et al. 2012. Allergology Int. 61:3-17). TSLP is described as responsible for the pruritis often present in atopic dermatitis and psoriasis. We demonstrate for the first time that a plant cell culture (PCC) extract of *Mimosa pudica* obtained by the process according to the invention has antioxidant and anti-inflammatory activities and shows in particular a very strong inhibition of TSLP in the in vitro model of atopic dermatitis. We also demonstrate that in the absence of mimosine in our extracts, a PCC extract of *Mimosa pudica* according to the invention retains the anti-inflammatory pharmacological activity.

The process for obtaining the preparation, the object of the present invention, consists in cellular dedifferentiation from plant material derived from *Mimosa pudica*, then in culturing suspended cells in the undifferentiated state in order to rapidly obtain a fine, abundant, homogeneous and sterile biomass of this plant. The cell culture makes the biosynthetic pathways of this plant more versatile at the cellular level.

The present invention therefore relates to a preparation derived from an in vitro culture of undifferentiated cells of *Mimosa pudica*, a cosmetic or dermatological composition comprising said preparation and uses thereof in cosmetology and/or dermatology and more preferentially for the treatment of inflammatory skin disorders, as antioxidant including the treatment of oxidative stress due to environmental pollution (tobacco, indoor and outdoor air pollution by chemical agents or allergens), and as anti-ageing agent.

Thus, the present invention concerns a process for in vitro preparation of a *Mimosa pudica* cell extract having a mimosine content of less than 5 ng/g dry weight, comprising the following steps:
  a. Provision of sterile plant material of *Mimosa pudica*,
  b. Dedifferentiation of cells from the plant material,
  c. Suspension culture of the undifferentiated cells in a liquid medium for maintaining them in the undifferentiated state,
  d. Propagation culture of an undifferentiated cell biomass in the culture medium,
  e. stopping the propagation and obtaining a cell extract having a mimosine content of less than 5 ng/g dry weight.

In a particular embodiment, the process according to the invention is characterized in that the *Mimosa pudica* plant material is selected from the group consisting of leaf, stem, petiole, root, seed, flower and bud.

In a particular embodiment, the process according to the invention is characterized in that step b) of dedifferentiation is carried out on a solid medium containing one or more growth factors.

In a particular embodiment, the process according to the invention is characterized in that the one or more growth factors include a hormone selected from the group consisting of auxins, cytokines, gibberellins and mixtures thereof.

In a particular embodiment, the process according to the invention is characterized in that step b) of dedifferentiation is repeated so as to obtain calluses of dedifferentiated cells.

In a particular embodiment, the process according to the invention is characterized in that step c) is carried out in a liquid medium containing one or more growth factors.

In a particular embodiment, the process according to the invention is characterized in that the one or more growth factors are the same as that or those of the dedifferentiation medium.

In a particular embodiment, the process according to the invention is characterized in that step d) of propagation culture is carried out by successive subcultures or dilutions in the liquid culture medium until a constant cell density is obtained.

In a particular embodiment, the process according to the invention is characterized in that it comprises the following additional steps:

f. liquid/solid separation, g. recovery of a cell extract consisting of biomass separated from the culture medium having a mimosine content of less than 5 ng/g dry weight.

In another particular embodiment, the process according to the invention is characterized in that it comprises the following additional steps:

f. liquid/solid separation, g. recovery of the cell extract consisting of the liquid phase of the culture medium having a mimosine content of less than 5 ng/g dry weight.

In a particular embodiment, the process according to the invention is characterized in that it comprises an additional step of crushing the extract and recovering a crushed cell material having a mimosine content of less than 5 ng/g dry weight.

In a particular embodiment, the process according to the invention is characterized in that the resulting crushed material is subjected to a liquid/solid separation followed by recovery of the liquid phase as cell extract having a mimosine content of less than 5 ng/g dry weight.

In another particular embodiment, the process according to the invention is characterized in that the resulting crushed material is subjected to a liquid/solid separation followed by recovery of the solid phase of cell debris as cell extract having a mimosine content of less than 5 ng/g dry weight.

In a particular embodiment, the process according to the invention is characterized in that the culture medium of step c) and/or step d) contains a phenyl-ammonia-lyase substrate.

In a particular embodiment, the process according to the invention is characterized in that the phenyl-ammonia-lyase substrate is selected from the group consisting of phenylalanine, in particular L-phenylalanine, cinnamic acid, aspartic acid, glutamic acid and mixtures thereof.

In a particular embodiment, the process according to the invention is characterized in that the resulting extract contains at least one N-phenylpropenoyl amino acid.

In a particular embodiment, the process according to the invention is characterized in that the N-phenylpropenoyl amino acid is selected from the group consisting of:

P1: 1-O-(4-coumaroyl)-β-D-glucose
$C_{15}H_{18}O_8$

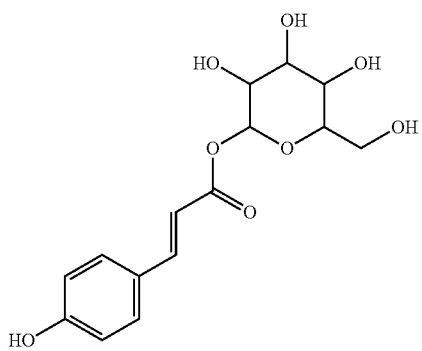 [SMILES: O=C(/C=C/c1ccc(O)cc1)OC1OC(CO)C(O)C(O)C1O]

P2: N-p-Coumaroylaspartic acid or Aspartic acid; (S)-form, N-(4-Hydroxycinnamoyl)
$C_{13}H_{13}NO_6$

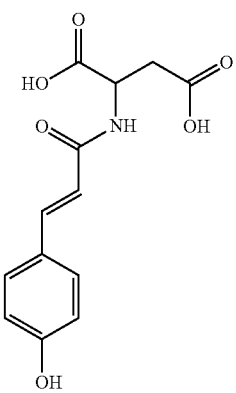 [SMILES: O=C(O)CC(NC(=O)/C=C/c1ccc(O)cc1)C(=O)O]

P3: N-cis-(p-Coumaroyl)glutamic acid or Glutamic acid; (S)-form, N-(4-Hydroxy-Z-cinnamoyl)
$C_{14}H_{15}NO_6$

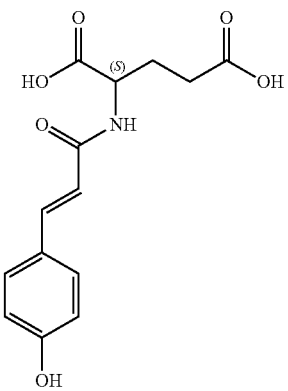

P5: 4-hydroxycinnamide
$C_9H_9NO_2$

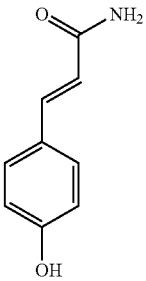

P6: Glutamic acid; (S)-form, N-cinnamoyl
$C_{14}H_{14}NO_5$

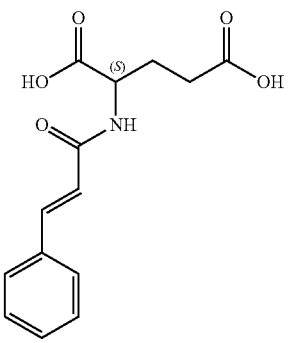

and mixtures thereof.

It is also an object of the present invention to provide an in vitro culture extract of *Mimosa pudica* cells obtainable by a process according to the present invention and having a mimosine content of less than 5 ng/g dry weight.

The invention also relates to an in vitro culture extract of *Mimosa pudica* cells, characterized in that its mimosine content is less than 5 ng/g dry weight.

In a particular embodiment, the in vitro culture extract of *Mimosa pudica* cells according to the invention is characterized in that it contains at least one N-phenylpropenoyl amino acid.

In a particular embodiment, the extract according to the invention is also characterized in that the at least one N-phenylpropenoyl amino acid is selected from the group consisting of:

P1: 1-O-(4-coumaroyl)-β-D-glucose
$C_{15}H_{18}O_8$

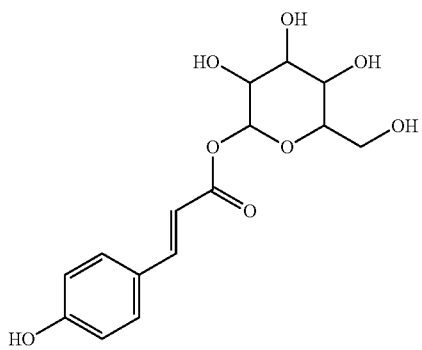 [SMILES: O=C(/C=C/c1ccc(O)cc1)OC1OC(CO)C(O)C(O)C1O]

P2: N-p-Coumaroylaspartic acid or Aspartic acid; (S)-form, N-(4-Hydroxycinnamoyl)
$C_{13}H_{13}NO_6$

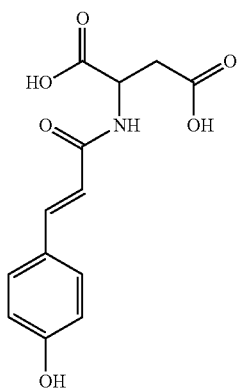 [SMILES: O=C(O)CC(NC(=O)/C=C/c1ccc(O)cc1)C(=O)O]

P3: N-cis-(p-Coumaroyl)glutamic acid or Glutamic acid; (S)-form, N-(4-Hydroxy-Z-cinnamoyl)
$C_{14}H_{15}NO_6$

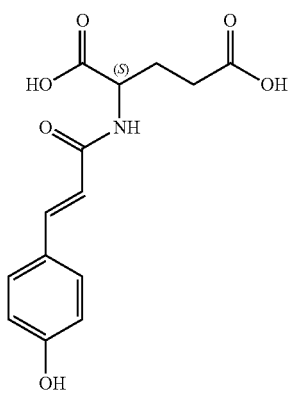

P5: 4-hydroxycinnamide
$C_9H_9NO_2$

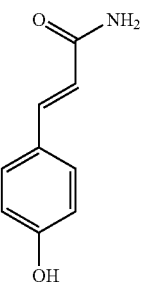 [SMILES: NC(=O)/C=C/c1ccc(O)cc1]

P6: Glutamic acid; (S)-form, N-cinnamoyl
$C_{14}H_{14}NO_5$

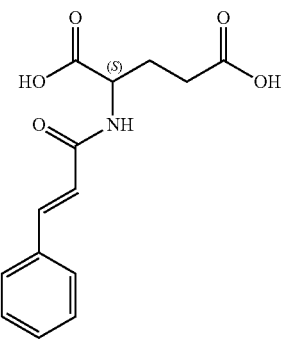

and mixtures thereof.

According to a particular embodiment, the extract according to the invention is characterized in that the total content of the extract in at least one N-phenylpropenoyl amino acid is comprised between 1 and 50 µg/g dry biomass, and more preferentially between 10 and 40 µg/g dry biomass.

According to a particular embodiment, the extract according to the invention is characterized in that the cells are undifferentiated cells.

Another object of the invention relates to an extract as described herein for use in the treatment of inflammatory skin disorders.

Another object of the invention relates to an extract as described herein for use as inhibitor of thymic stromal lymphopoietin.

In a particular embodiment, the inflammatory skin disorders are selected from atopic dermatitis, pruritus and psoriasis.

A composition for use as inhibitor of thymic stromal lymphopoietin comprising an extract according to the invention is also an object of the invention.

A dermatological composition for the treatment of an inflammatory skin disorder selected from atopic dermatitis, pruritus and psoriasis, comprising an extract according to the invention in an effective amount and at least one dermatological excipient is also an object of the present invention.

The present invention also relates to the use of an extract according to the invention and as described herein for the cosmetic treatment of skin ageing and of skin disorders associated with skin oxidative stress, including oxidative stress due to environmental pollution.

The present invention also concerns a cosmetic composition comprising an extract according to the invention combined with a cosmetically acceptable excipient.

The invention also relates to a dermatological composition comprising an extract according to the invention as described, combined with a dermatologically acceptable excipient.

Finally, the present invention also concerns the use of a composition according to the invention for the cosmetic treatment of skin ageing and of skin disorders associated with skin oxidative stress, such as oxidative stress due to environmental pollution.

DEFINITIONS

The expression "dedifferentiation" refers to a return of cells to a meristematic state, i.e. to the state of undifferentiated cells, i.e. cells which have lost their morphological characteristics and are physiologically different from cells of the original tissue of which they were part.

In one embodiment of the invention, the extract has a mimosine content of less than 5 ng/g dry weight, more particularly less than 4 ng/g dry weight, even more particularly less than 3 ng/g dry weight, still more particularly less than 2 ng/g dry weight, or even more particularly less than 1 ng/g dry weight.

It is therefore particularly remarkable and surprising that the culture according to the invention of Mimosa pudica cells in the undifferentiated state makes it possible to obtain an extract practically devoid of mimosine, and this is the whole point of the present invention because of the toxicity of this compound.

In the context of the present invention, the term "extract" equally relates to the culture medium, once the propagation of the culture has stopped, mainly composed of undifferentiated Mimosa pudica cells immersed in the liquid culture medium. Such an extract contains between 100 and 500 g dry weight per litre, particularly between 150 and 350 g/l. The material being mainly composed of the biomass of undifferentiated cells.

The extract according to the invention also relates to the solid fraction of said culture medium, i.e. the biomass consisting of undifferentiated Mimosa pudica cells separated from the culture medium.

The extract according to the invention also relates to the liquid fraction of said culture medium, i.e. the culture medium cleared of undifferentiated Mimosa pudica cells.

These solid and liquid fractions can be easily obtained by a liquid/solid separation technique well known to the skilled person, which may be selected from centrifugation, settling, filtration for example.

The extract according to the invention may also consist of crushed undifferentiated Mimosa pudica cells. Such crushed material may be obtained directly by crushing the culture medium after stopping the propagation. Such a crushed material therefore contains the membrane and cell wall debris, the intracellular contents as well as the culture medium and the entrained compounds and molecules.

Such a crushed material making up the extract according to a particular embodiment may be obtained by crushing the solid fraction of the culture medium, consisting of the undifferentiated Mimosa pudica cells, as obtained above, as well as the entrained compounds and molecules.

An extract according to the invention may also consist of the solid fraction of the crushed material as defined above. Such an extract comprises the cell wall and membrane fragments as well as certain entrained compounds and molecules.

Finally, an extract according to the invention may be represented by the liquid fraction of the crushed material after resuspension and crushing of the solid fraction of the culture medium containing the undifferentiated Mimosa pudica cells.

Crushing can be carried out by any means known to the skilled person, using an Utra-Turrax type mixer for example, or by shaking with glass beads, optionally assisted by ultrasound, for example.

It thus emerges that the extract according to the invention may take several forms.

Preferably, the extract according to the invention contains whole undifferentiated Mimosa pudica cells or crushed undifferentiated Mimosa pudica cells. This extract is characterized by its mimosine content of less than 5, preferentially less than 4, preferentially less than 3, more particularly less than 2, even more particularly less than 1 ng/g dry weight.

In the context of an extract according to the invention consisting of a liquid fraction devoid of solid fraction (whole cells or cell fragments), the amount of mimosine is less than 5, preferentially less than 4, preferentially less than 3, more particularly less than 2, even more particularly less than 1 ng/ml extract.

More generally, in vitro cultures of suspended plant tissues can be used to produce active organic compounds derived directly from the primary or secondary metabolism of the cells.

The suspended plant cells are maintained totipotent in an undifferentiated state similar to that of stem cells for animal cell cultures. These plant cells are therefore theoretically capable of producing all the metabolites observed in the whole plant. Dedifferentiation causes a disruption of biosynthetic pathways of a genetic or epigenetic nature so that the chemical profiles differ quantitatively and qualitatively between the whole plant and the resulting cell lines. Thus, theoretically, reaction intermediates not observed in the whole plant may appear in cell suspension and vice versa. This provides a new resource and allows access to latent phytochemical biodiversity.

One of the objects of the present invention concerns the preparation derived from an in vitro culture of undifferentiated Mimosa pudica cells.

"Undifferentiated" or "dedifferentiated" plant cells means any plant cell not having any character of a particular specialization, i.e. in a physiological state close to the meristematic tissues of the plant in the natural state. These cells are able to live by themselves and without dependence on other cells.

The initial dedifferentiation of Mimosa pudica cells is obtained from living plant material taken from the plant or young shoot, whether leaf, petioles, stem, root, seed, flower or its organs or bud, more particularly from seeds or leaves.

The process for culturing dedifferentiated cells is obtained in vitro by any method known to the person skilled in the art, for example by referring to Murashige, T., Skoog, F. 1962. A revised medium for rapid growth and bio assays with tobacco tissue cultures. Physiol. Plant 15: 473-496/Plant Culture Media, Vol-1 Formulations and Uses E. F. George, D. J. M. Puttock, and H. J. George (1987) Exegetics Ltd. Edington, Westbury, Wilts, BA134QG England.

An extract according to the present invention may be obtained by carrying out the following successive steps:
 a) dedifferentiation of the cells,
 b) preparation of a cell suspension with a culture medium maintaining the cells in an undifferentiated physiological state,
 c) propagation culture and biomass production with a culture medium
 d) in a particular embodiment, enrichment of the intracellular compartment of the culture with metabolites of interest by bioconversion
 e) obtaining the extract.

The preparation can be carried out in an Erlenmeyer flask if the objective is to produce small amounts of biomass, or in a bioreactor for larger amounts. For example, the average amount harvested in an Erlenmeyer flask with 500 ml of cell suspension is 175 g of dry biomass (or 350 g biomass per L cell suspension), while the average harvested in a 10 L bioreactor is 3000 g of dry biomass (300 g/L biomass).

Depending on the cultured species and their sensitivity to culture stress, different types of bioreactors can be used to improve tissue growth and secondary metabolite production. Three main modes are encountered for culturing plant cells in a bioreactor:
1. discontinuous or batch culture,
2. recharge/harvest or fed-batch culture and
3. continuous culture.

Plant Material Sterilization Step:

*Mimosa pudica* explants, and more particularly seeds, are collected and decontaminated with 70% ethanol solutions then sodium or calcium hypochlorite solutions or mercury chloride solutions at room temperature for several minutes. The tissues are rinsed with sterile distilled water then washed at least once with sterile distilled water at the end of decontamination.

Cell Dedifferentiation Step

If seeds are used, they are decontaminated and germinated with a Murashige & Skoog nutrient agar medium, supplemented with sucrose and growth factors. The latter will condition the cellular machinery of the explants so as to stimulate cell division and produce dedifferentiated cell clusters or calluses (callogenesis). The callus obtained will be transferred to fresh dedifferentiation nutrient medium every 3 to 4 weeks. Indeed, certain components of this agar medium may be metabolized by the calluses or degraded by the action of the air.

A skilled person may also use differentiated tissues such as explants from leaves, for example, to obtain undifferentiated cells.

In general, in order to obtain rapid dedifferentiation and intense cell multiplication in the form of friable calluses (callogenesis) that will promote transfer to liquid medium, a hormonal composition based on growth factors such as auxins (picloram or 4-amino-3,5,6-trichloro-2-pyridinecarboxylic acid) and cytokinins (kinetin) has been successfully tested. Sterilized seeds can be placed in contact with the agar medium composed of a medium of 30 g/L sucrose, 8 g/L agar, supplemented with 1.5 mg/L kinetin and 2 mg/L 4-amino-3,5,6-trichloro-2-pyridinecarboxylic acid (picloram) and adjusted to pH 6 before autoclaving for 20 min at 121° C. (1 bar). Petri dishes containing the seeds are incubated in the dark at 28° C. The first calluses appear after a few days, in particular 2 weeks. The resulting calluses are transferred to fresh medium approximately every 3-4 weeks by dividing the calluses with a scalpel so as to maintain a size of about 2 to 3 cm. These transfers continue for about several weeks, or even several months, for example 6 to 8 months, so as to obtain friable calluses.

Step of Preparing a Cell Suspension in a Culture Medium

Cell dedifferentiation by successive transfers of calluses on agar medium leads to the formation of friable calluses. This decrease in cohesion between the cells is a consequence of the dedifferentiation which may occur at between two and six months depending on the plant. This state is favourable to transfer to liquid medium because it guarantees disintegration of the calluses in cell suspension while minimizing induced mechanical stresses. Thus, a collection of friable calluses is introduced (10-20% by volume) into the liquid nutrient medium prepared using the same formulation as the dedifferentiation agar medium but without gelling agent.

The friable calluses are thus disintegrated in liquid medium by the action of a shaking table for several days and the resulting cell suspension is cleared of the non-disintegrated callus parts, thus forming a homogeneous cell suspension. This suspension is cultured so as to obtain a sufficiently dense cell population. At this stage the suspension is (subcultured or) diluted in fresh nutrient medium and cultured in the same way.

The initial cell suspension can be prepared by placing about 20 to 40 g of friable calluses in a 500 ml Erlenmeyer flask containing 200 ml of medium. The friable calluses are disintegrated in liquid medium by the action of a shaking table for 2 to 3 days at 115 rpm in the dark at 29° C. Next, the cell suspension is collected with a pipette, leaving out the non-disintegrated residual callus clusters. The cell suspension thus forms a homogeneous suspension of cell microclusters. This suspension is cultured so as to obtain a "sufficiently" dense cell population. The resulting cell suspension is cultured for 14 days and then propagated by dilution to ⅕th in fresh medium for the same amount of time. The composition of the culture medium (nutrients, growth factors, etc.) was adjusted to maximize biomass productivity. The result is the SENSMS biomass propagation medium (see Table 1) optimized for liquid cell suspension. This medium is a modified version of the Murashige & Skoog medium for callogenesis. This medium is adjusted to pH 6 by adding KOH followed by autoclaving for 20 min at 121° C. (p=1 bar) or 0.2 μm sterilizing filtration.

TABLE 1

SENSMS medium, which is a modified version of the Murashige & Skoog (MS) medium used for suspension culture of sensitive cells in an Erlenmeyer flask or a bioreactor under optimal conditions
SENSMS medium - optimized for cell growth

| | | | |
|---|---|---|---|
| $NH_4NO_3$ | 1.65 | g/L | Macro elements |
| $KNO_3$ | 1.9 | g/L | |
| $CaCl_2 \cdot 2H_2O$ | 0.44 | g/L | |
| $MgSO_4 \cdot 7H_2O$ | 0.37 | g/L | |
| $KH_2PO_4$ | 0.17 | g/L | |
| KI | 0.83 | mg/L | Micro elements |
| $H_3BO_3$ | 6.2 | mg/L | |
| $MnSO_4 \cdot 4H_2O$ | 22.3 | mg/L | |
| $ZnSO_4 \cdot 1H_2O$ | 6.61 | mg/L | |
| $Na_2MoO_4 \cdot 2H_2O$ | 0.25 | mg/L | |
| $CuSO_4 \cdot 5H_2O$ | 0.025 | mg/L | |
| $CoCl_2 \cdot 6H_2O$ | 0.025 | mg/L | |
| $FeSO_4 \cdot 7H_2O$ | 41.7 | mg/L | |
| $Na_2EDTA \cdot 2H_2O$ | 55.95 | mg/L | |
| myo-Inositol | 150 | mg/L | Vitamins |
| Nicotinic acid | 0.75 | mg/L | |
| Pyridoxine-HCl | 0.75 | mg/L | |
| Thiamine-HCl | 0.75 | mg/L | |
| Glycine | 2 | mg/L | |
| Picloram | 2 | mg/L | Factors (growth hormones) |
| Kinetin | 1.5 | mg/L | |
| Sucrose | 30 | g/L | Carbon source |

Propagation Culture and Biomass Production with a Culture Medium

After several such subcultures, the cell suspension is stabilized when the cell density obtained over the period is constant. Adjustments to the composition of the culture medium (nutrients, growth factors, etc.) are then possible in order to maximize biomass productivity. This optimized medium is used as biomass production means in order to extract the active principles.

The cell culture under "optimal" conditions thus established is stabilized and maintained in an Erlenmeyer flask (propagation culture) with a ⅕th dilution of the cell suspension every 14 days. This is equivalent to a cell culture inoculated with approx. 60 g/L of fresh biomass that produces a cell suspension of approx. 350 g/L after 14 days of culture; or inoculated in a bioreactor as needed.

The fresh biomass represents 100 to 500 g per litre of suspension, and more preferably between 200 and 350 g per litre of suspension.

Optional Step: Enrichment of the Intracellular Compartment of the Culture in Metabolites of Interest by Bioconversion It is sometimes essential to provide cells with "precursors" whose structure is sufficiently close to the final product in the hope that they will be incorporated, modified or transformed using the enzymatic machinery present in the cell.

In a particular embodiment, the process according to the invention is characterized in that the culture medium of step c) and/or step d) contains a phenyl-ammonia-lyase substrate.

In a particular embodiment, the process according to the invention is characterized in that the phenyl-ammonia-lyase substrate is selected from the group consisting of phenylalanine, in particular L-phenylalanine, cinnamic acid, aspartic acid, glutamic acid and mixtures thereof.

In a particular embodiment, the process according to the invention is characterized in that the resulting extract contains at least one N-phenylpropenoyl amino acid.

This process of modification of a precursor by the cell is called bioconversion. The addition of precursors to the culture medium may be an interesting approach to increase the production of secondary metabolites of interest. This concept is based on the principle that any compound that is a reaction intermediate in the biosynthetic pathway of the metabolite of interest may probably improve the yield of the final product.

Thus, based on the structure of NPAs (see Figure below), certain molecules (amino acids) appear to be precursors of these reaction intermediates. For example, the amino acid L-phenylalanine is a useful precursor for positively modulating the activity of a phenyl-ammonia-lyase (PAL) enzyme. Similarly, cinnamic acid may be at the origin of this same phenomenon. Multiple combinations may also be contemplated, notably with aspartic acid or glutamic acid. We have performed many experiments using these various precursors (alone or in combination) and, surprisingly, with L-phenylalanine we obtain useful NPAs that have never been described in *Mimosa pudica* cells such as:

P1: 1-O-(4-coumaroyl)-β-D-glucose
$C_{15}H_{18}O_8$

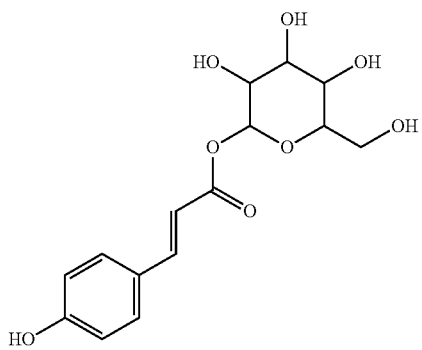 [SMILES: O=C(/C=C/c1ccc(O)cc1)OC1OC(CO)C(O)C(O)C1O]

P2: N-p-Coumaroylaspartic acid or Aspartic acid; (S)-form, N-(4-Hydroxycinnamoyl)
$C_{13}H_{13}NO_6$

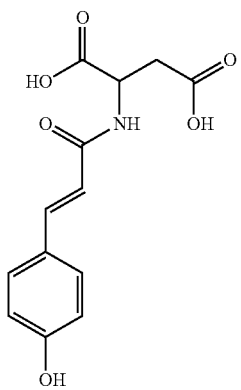 [SMILES: O=C(O)CC(NC(=O)/C=C/c1ccc(O)cc1)C(=O)O]

P3: N-cis-(p-Coumaroyl)glutamic acid or Glutamic acid; (S)-form, N-(4-Hydroxy-Z-cinnamoyl)
$C_{14}H_{15}NO_6$

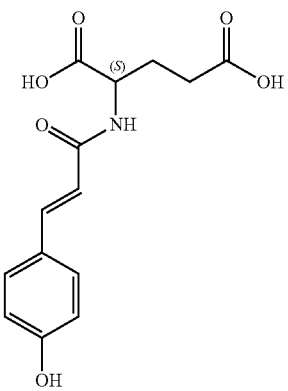

P5: 4-hydroxycinnamide
$C_9H_9NO_2$

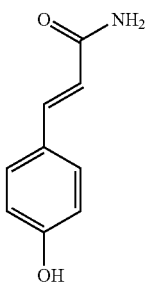 [SMILES: NC(=O)/C=C/c1ccc(O)cc1]

P6: Glutamic acid; (S)-form, N-cinnamoyl
$C_{14}H_{14}NO_5$

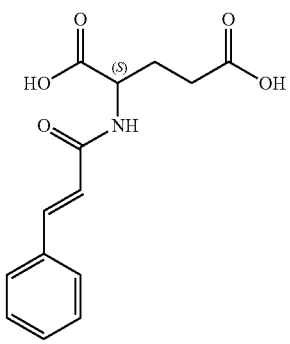

and mixtures thereof.

Obtaining the Extract

After stopping the propagation, the resulting cell suspension may be filtered or centrifuged to separate it from the culture medium and obtain both the extracellular medium (or culture supernatant) and the harvested biomass. The biomass may then be treated in different ways depending on the use. It is either dried by freeze-drying or resuspended, for example at 30% in 68.2% glycerine with 0.8% carrageenan and 1% citric acid. Solvent extraction may also be carried out on the cell suspension by first performing cell dispersion by sonication or by French press for example.

Formulation

Another object of the invention concerns a cosmetic or dermatological composition comprising an in vitro culture extract of *Mimosa pudica* cells obtainable by the process according to the invention and one or more cosmetically and/or dermatologically acceptable excipients, preferably intended for topical application.

The cosmetically and/or dermatologically acceptable excipients may be any excipient amongst those known to the person skilled in the art. The composition according to the invention will notably be a topical composition notably in the form of cream, lotion, gel, ointment, emulsion, micro-emulsion, spray, etc.

The cosmetic or dermatological composition according to the invention may in particular contain additives and formulation aids, such as emulsifiers, thickeners, gelling agents, water fixatives, spreading agents, stabilizers, dyes, fragrances and preservatives.

Another object according to the invention is the use of an extract according to the invention in the treatment of treatments of inflammatory skin disorders, as antioxidant including the treatment of oxidative stress due to environmental pollution, and as anti-ageing agent.

"Inflammatory skin disorder" means atopic dermatitis, pruritus, and itching due to pruritus (TSLP inhibition), eczema and psoriasis.

Preferably, said dermatological inflammatory disorders consist of atopic dermatitis, pruritus, eczema or psoriasis. According to another embodiment, the invention concerned by the present patent application relates to a composition comprising at least, as active principle, an extract according to the invention.

The invention therefore preferably relates to a cosmetic or dermatological composition. The composition according to the invention is intended for the treatment of dermatological inflammatory disorders.

Preferably, said dermatological inflammatory disorders consist of atopic dermatitis, pruritus, itching due to pruritus, eczema or psoriasis.

The composition according to the invention may be prepared in the form of a water-in-oil (W/O) or oil-in-water (O/W) emulsion, a multiple emulsion such as for example, a water-in-oil-in-water (W/O/W) emulsion or an oil-in-water-in-oil (O/W/O) emulsion, a micro-emulsion or else in the form of a hydrodispersion or a lipodispersion, a gel or an aerosol. The dermatologically or cosmetically compatible excipients may be any excipient amongst those known to the person skilled in the art with a view to obtaining a composition for topical application in the form of milk, cream, balm, oil, lotion, gel, foaming gel, ointment, spray, etc.

In addition to dermatological and cosmetic compositions, the invention also relates to pharmaceutical compositions for use as a medicinal product.

The invention thus relates to a pharmaceutical composition further comprising a pharmaceutically acceptable carrier. In the present description, a pharmaceutically acceptable carrier is defined as a compound or a combination of compounds contained in a pharmaceutical composition that does not cause side reactions and that, for example, facilitates the administration of the active compound(s), increases its shelf life and/or efficacy in the body, increases its solubility in solution or improves its storage. These pharmaceutically acceptable carriers are well known and will be adapted by the person skilled in the art according to the nature and mode of administration.

EXAMPLE: PLANT CELL CULTURE IN A WAVE BIOREACTOR (5 L)

Materials and methods: The WAVE reactor (Sartorius) with a useful volume of 5 L containing 4 L of MS SENS medium (see table above for composition) was inoculated with 1 L of *M. pudica* cell culture suspension (cell density between 300 and 400 g/L in fresh weight (FW))

Parameters:
Temperature: 27° C.
Air volume: 0.5 L/min (lpm)
Pressure: 5 mPa to 10 mPa
Rocking angle: 7°.
$pO_2$ maintained at 75% by increasing rpm between D0 (19 rpm) and D9 (27 rpm)
$pO_2$ maintained at 75% by enriching the air with $O_2$ between D9 (5% $O_2$) and D15 (20% $O_2$) at 25 rpm By following the growth kinetics, an increase in biomass evaluated by fresh weight (FW) or dry weight (DW), correlated with sugar consumption (decrease in the curve), is observed until the 13$^{th}$ day of culture, D13, when the bioconversion medium is added.

Bioconversion and Harvesting

After 13 days (D13) of batch culture of a 4 L culture, the cell concentration is between 300 and 350 g/L (FW), equivalent to 12 to 14 g/L (DW). When this cell concentration is reached, bioconversion is carried out by injecting the precursors by sterilizing filtration: we have selected the various amino acids (aspartic acid, cinnamic acid, glutamic acid or L-phenylalanine), and under our culture conditions, L-phenylalanine gave the best results in terms of NPA bioconversion yield. Below is an example of the following precursor concentrations:

| Extemporaneous preparation | Concentration (DW | Concentration (Suspension) | Final volume of DW (ml) |
|---|---|---|---|
| $NH_4H_2PO_4$ | 50 g/L | 0.1 g/L | 10 |
| L-Phenylalanine | 300 mM | 6 mM | 100 |
| Sucrose | 500 g/L | 10 g/L | 100 |

Bioconversion Medium Favouring Hydroxycinnamic Acids Including their Derivatives, N-phenylpropenoyl Amino Acids (NPAs)

Dilute the compounds in $H_2O$ and add the mix to the bioreactor by sterilizing filtration. After 48 h, i.e. between D15 and D16, harvest the biomass by direct filtration using a "20 μm nylon bag" for example. The biomass is washed once with a volume of sterile demineralized water equivalent to the volume of biomass harvested. The cell concentration evaluated at D13 must be equivalent (+/−10%) to D15. Throughout the culture, the decrease in suspension volume is mainly due to the samples taken.

A volume of the culture is taken at D13, D14, D15 and D16, then extracted with a solvent and the various extracts are dissolved in before being analysed by HPLC coupled with mass spectrometry. The figure shows, relative to D13 (the day the precursor L-phenylalanine was added), the gradual appearance of the new peaks D14, D15 until the maximum intensity is reached at D16.

Peaks P1, P2, P3, P4, P5 and P6 were isolated at D16, analysed by mass spec. and NMR to determine the structure of the molecules. Peak P4 being in a very small amount, we were unable to determine its structure. For the first time, and surprisingly, we discover that the precursor L-phenylalanine was the best amino acid for bioconversion.

NPA products P1, P2, P3, P5 and P6 were identified by mass spectroscopy and NMR.

List of NPA Names:
P1: 1-O-(4-coumaroyl)-β-D-glucose
$C_{15}H_{18}O_8$

P2: N-p-Coumaroylaspartic acid or Aspartic acid; (S)-form, N-(4-Hydroxycinnamoyl)
$C_{13}H_{13}NO_6$
P3: N-cis-(p-Coumaroyl)glutamic acid or
Glutamic acid; (S)-form, N-(4-Hydroxy-Z-cinnamoyl)
$C_{14}H_{15}NO_6$
P5: 4-hydroxycinnamide
$C_9H_9NO_2$
P6:
Glutamic acid; (S)-form, N-cinnamoyl
C14H14NO5

EXAMPLE 2: ASSAYS OF MIMOSINE IN MIMOSA PUDICA PLANT CELLS Versus Leaves

The objective is to develop the analytical conditions for identifying and quantifying mimosine in the extracts. Biomass derived from suspension culture of *M. pudica* cells (with bioconversion) was extracted with ETOH80 or ETOH60. Dried leaves of *M. pudica* were dried, crushed and extracted with the same solvents. L-Mimosine from Sigma is used as reference for identification and quantification. The samples were analysed by HPLC/mass spectrometry.
Materials and Methods: Analytical Conditions
  ABSciex TripleTOF 4600 mass spectrometer
  Method (ES+): TOF (100 ms)/MRM (50 ms)
  Column: Acquity HSS C18, 1.8 µm, 2.1×100 mm, sintered 0.5 µm
  Eluents: A ($H_2O$-0.1% $HCO_2H$)/B ($CH_3CN$-0.1% $HCO_2H$)
  Flow rate: 500 µl/min
  Injections: 10 µl
  Gradient:

| Time (min) | % A | % B |
|---|---|---|
| 0.0 | 100 | 0 |
| 1.0 | 100 | 0 |
| 4.0 | 10 | 90 |
| 4.01 | 0 | 100 |
| 5.0 | 0 | 100 |

The quantitative assays established that the lower limit of quantification (LLOQ) reached in the control solution is 5 ng/mL. This LLOQ and the preparation method of our hydro-ethanolic samples confirm the absence of mimosine in our cell culture samples at the limit of detection (1 ng of mimosine per g of biomass):
  EtOH80 and EtOH60 extracts of cells (20% w/w)<1 ng/g of fresh cells
  EtOH60 extract of freeze-dried cells (5% w/w)<1 ng/g of freeze-dried cells
  EtOH60 extract of plants=2160 ng/g of dry plant.
  EtOH80 extract of plants=780 ng/g of dry plant
The analyses were carried out in the same way on the PCCs without bioconversion (i.e. without addition of NPA precursors) and showed that the mimosine content is also <1 ng/g of fresh or freeze-dried cells.

In conclusion, in our *M. pudica* plant cell cultures, surprisingly, we did not detect any undesirable element such as mimosine.

EXAMPLE 2—ANTI-INFLAMMATORY ACTIVITIES: COMPARISON OF PLANT EXTRACT VS. PCC Extract In this example, we compare the anti-inflammatory activity of 2 *Mimosa pudica* extracts (E11 and E13). Extract E11 comes from ethyl acetate extraction of the dried and crushed *Mimosa pudica* leaves and extract E13 comes from extraction with the same solvent of the crushed materials derived from *Mimosa pudica* plant cell culture without bioconversion in an Erlenmeyer flask. The 2 extracts were weighed after evaporation of the solvent to dryness. They were taken up in DMSO. To evaluate and compare the anti-inflammatory activity of the 2 extracts in the same concentrations, we have an in vitro pharmacological test which consists in stimulating murine macrophages, RAW264.7 cells, that express on their surface the TLR4 receptor by the bacterial LPS according to (Kang et al. 2002. J Pharmacol Exp Ther. 302:138-144). Several parameters were studied and compared to a reference anti-inflammatory, dexamethasone:
  nitrite production by the Griess technique. The nitrite level reflects the level of NO synthesis induced by inducible nitrite oxide synthase (iNOS).
  cytokine secretion: interleukin-6 by ELISA
  TNF-alpha production by multiplex assay
Cell Culture
RAW264.7 cells are mouse macrophages in lineage. These cells are adherent and cultured in a 12-well plate at 100000 cells/$cm^2$ (Millipore Scepter count) in DMEM medium supplemented with 10% FCS, 2 mM L. glutamine and 50 µg/mL gentamicin.

At about 70% confluence, the cells are treated with *Mimosa pudica* extracts E11 (plant) or E13 (PCC) in the same concentrations (dry weight) or with the reference anti-inflammatory 1 µM dexamethasone (Biovison 1042-1) 1 h before being activated by 0.2 µg/mL [*E. coli* 055:B5] LPS. The cells are incubated at 37° C. under 5% CO2. After 24 h, the cell supernatants are recovered in ice, centrifuged for 5 min at 3000 rpm at 4° C., aliquoted then stored at −80° C. The cell tests were repeated 3 times, including twice in duplicate. The average values of the results are presented in the graphs.

Cell viability is monitored by a metabolic test with MTT (3-[4,5-dimethylthiazol-2yl]-2,5-diphenyltetrazolium bromide) using the SIGMA CGD1 Kit (kit based on the activity of an enzyme, mitochondrial succinate dehydrogenase). This test was done beforehand to determine the doses of the extracts to be tested in this model.
Nitrite Assay
The level of NO synthesis is evaluated in fresh or frozen (−80° C.) cell supernatants, without affecting the assay. The principle of the assay is based on the Griess (diazotization) reaction which produces a pink azo compound with absorbance at 540 nm.
IL6 Assay
IL-6 is assayed in the cell supernatants diluted to $\frac{1}{200}^{th}$ by colorimetric ELISA, according to the supplier's protocol (R&D Systems, kit M6000B).
TNF Alpha Assay
Simultaneous assay of TNF-alpha in the cell supernatants was performed using the Luminex xMAP (multi-analyte profiling) technology which is based on the principles of flow cytometry and ELISA in a 96-well microplate. The microbeads used as substrate incorporate two fluorochromes in a precise ratio, which gives them an identifying colour code (different fluorescences). The optical system of the cytometer (Bio-Plex 200) consists of two lasers: a red laser (λ=635 nm) excites in each microbead its defining dye mixture, and thus identifies the cytokine to be assayed. The second laser, green, (λ=532 nm) excites the reporter fluorochrome attached to the specific detection antibody in order to quantify the cytokine. The system is controlled by a computer equipped with data acquisition and analysis software (Bio-Plex Manager version 4.1).

After thawing, the supernatants were tested diluted to $1/10^{th}$ and $1/40^{th}$ in culture medium, using a Milliplex Kit (MILLIPORE, item number MCYTOMAG-70K-04). The latter includes specific beads, detection antibodies and standards for assaying cytokines.

Results

Concentrations are expressed as averages. The inhibition percentages, when cited for the extracts, are relative to the 0.2% DMSO control. DMSO is used to dissolve the dry sample beforehand, before dilution in aqueous buffer for the cell tests.

Figure 2:
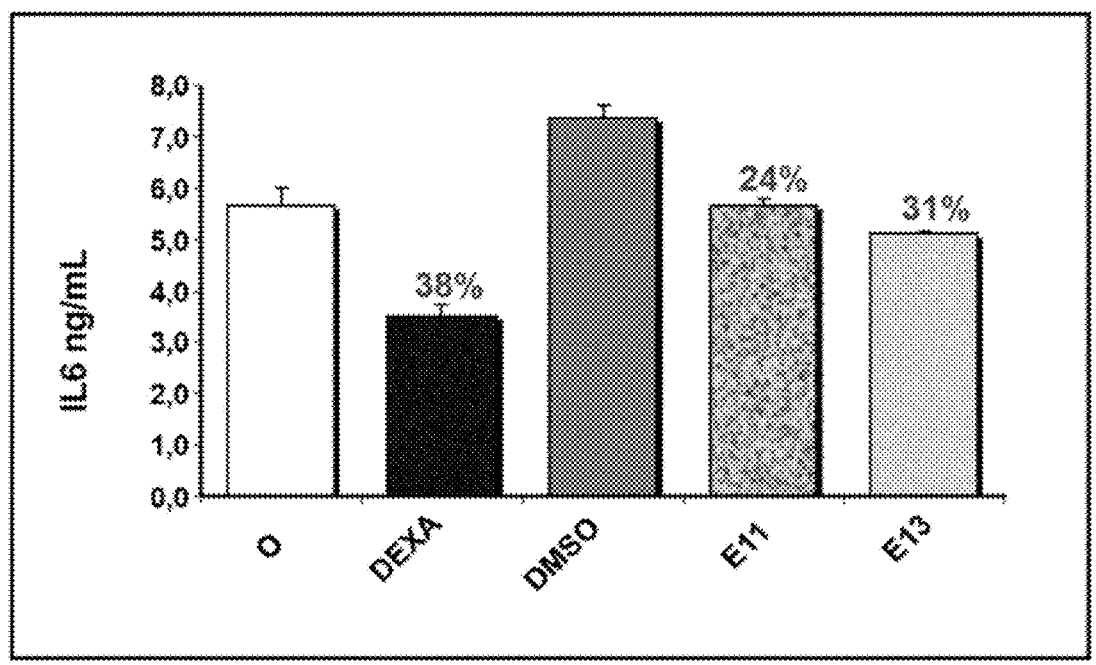
Figure 3:
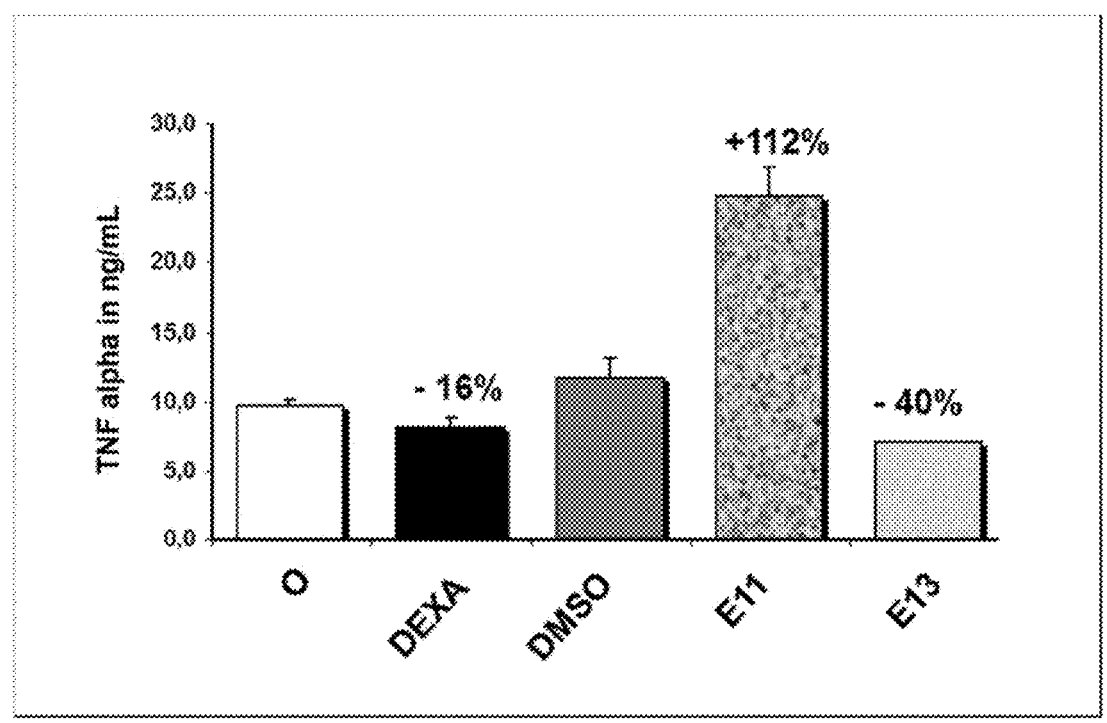

Figure Legends:
- FIG. 1: NITRITE ASSAY
- FIG. 2: IL6 ASSAY
- FIG. 3: TNF-alpha ASSAY The various samples are listed on the X-axis (from left to right):
- O: negative control—culture of RAW246.7 cells activated by 0.2 μg/mL LPS.
- DEXA: positive control—incubation of cells with 1 μM dexamethasone (Biovison 1042-1) 1 h before being activated by 0.2 μg/mL LPS.
- DMSO: incubation with the solvent control used to solubilize (E11 and E12) 1 h before being activated by 0.2 μg/mL LPS.
- E11: incubation with extract derived from *M. pudica* leaves (50 μg/mL) 1 h before being activated by 0.2 μg/mL LPS.
- E13: with extract derived from plant cells (50 μg/mL) 1 h before being activated by 0.2 μg/mL LPS.

Nitrite Assay

NO production is exclusively inducible and significantly inhibitable by dexamethasone (% i=35). 0.2% DMSO has no impact on the assay. Plant extract E11 weakly inhibits (% i=16%) nitrite production while the extract E13 inhibits nitrite production in an equivalent way and close to the inhibition obtained with the reference anti-inflammatory (% i=32%).

IL-6 ELISA

Cells activated (O) with LPS secrete IL6. Dexamethasone (DEXA) inhibits IL-6 secretion (% i=38%). The extracts inhibit IL-6 secretion for E11 (% i=24%) and for E13 (% i=31%)

Luminex Assay of TNF-Alpha

RAW264.7 cells secrete TNF-alpha in the basal state (0.23 ng/mL on average). This production is activated by 0.2 μg/mL LPS up to 10 ng/ml TNF-alpha. This activation is weakly inhibitable by dexamethasone (% i=16%). PCC extract E13 reduces TNF-alpha production (% i=40%). Conversely, plant extract E11 increases TNF-alpha production and seems to potentiate the activity of LPS (+112%).

In conclusion, the results show that the 2 extracts E11 and E13 at the same concentration strongly inhibit inflammation, reflected in this model by: inhibition of nitrites NO, inhibition of pro-inflammatory cytokine IL6 like the control, DEXA. Surprisingly, under these experimental conditions, PCC extract E13, better than DEXA, inhibits TNF-alpha while plant extract E11 potentiates it.

EXAMPLE 3: ANTIOXIDANT ACTIVITY—ORAC TEST

Antioxidant activity was evaluated using an oxygen radical absorbance capacity (ORAC) test (Dévalos A. et al.; Polish journal of food and nutrition sciences; 2003; 12/53: 133-136). The ORAC value is used to evaluate the antioxidant capacity of an extract. AAPH (2,2'-azobis-2-methylpropanimidamide, dihydrochloride) is the source of peroxyl free radicals. In this test it is used to mimic the kinetics of fluorescein degradation by free radicals. This results in a decrease in fluorescence over time and the concentration of the extract or reference tested (here Trolox). Trolox (an analogue of vitamin E) is known as a strong antioxidant. The addition of Trolox (standard solutions) or extract protects fluorescein from degradation. This makes it possible to evaluate an anti-oxidant activity measured against Trolox standard solutions.

Extracts of *Mimosa pudica* PCC with a bioconversion step (NPAs). Batch WO2. Samples taken on D13, bioconversion day, on D14 at 10 am, on D14 at 4 pm, D15, 16 and D17.

Dilution of sampled extracts in water.

ORAC Test

Solutions used: all solutions are prepared in phosphate buffer 75 mM, pH 7.6. 1.17 μM fluorescein (use of a 117 mM stock solution, storage 1 week at 4° C.). 125 mM AAPH to be prepared extemporaneously. 1 mM Trolox (storage −20° C.)

Preparation of Trolox Standard Solutions:

| Tubes | 1 mM Trolox (μl) | Phosphate buffer (μl) | Trolox [ ] in μM | pmoles of Trolox |
|---|---|---|---|---|
| 1 | 40 | 960 | 40 | 800 |
| 2 | 30 | 970 | 30 | 600 |
| 3 | 20 | 980 | 20 | 400 |
| 4 | 10 | 990 | 10 | 200 |
| 5 | 5 | 995 | 5 | 100 |
| 6 | 2.5 | 997.5 | 2.5 | 50 |
| 7 | 0 | 1000 | 0 | 0 |

Reaction volume: 200 μl

Place the following in a black 96-well plate: 20 μl of antioxidant (Trolox standard solutions or extract to be tested (crushed cell culture medium))+160 μl of 1.17 μM fluorescein. Incubate the film-covered plate 15 min at 37° C. Add 20 μl of 125 mM AAPH/well. Immediately incubate at 37° C. in a spectrofluorometer (SpectraMax) and take a reading every minute for 90 min at an excitation wavelength of 485 nm and an emission wavelength of 520 nm. Each test is carried out in triplicate. Calculate the areas under the curve (AUCs) for each of the tests (Trolox standard solutions or samples). Determine net AUCs=AUC standard solution point or sample—blank AUC. Plot the calibration curve: Trolox concentration (μM) as a function of net AUC.

The linear equation is used to determine a Trolox equivalent (μM) for each of the samples assayed.

Eq Trolox in μM=$a$×(Auc net)2+$b$×(AUC net)

(a and b of which are determined by the linear equation).

The ORAC value corresponds to pmoles Trolox/100 g extract

ORAC value (TEAC)=Trolox eq in μM×20×(100 000/[of the extract tested]×20)

Figure 4:
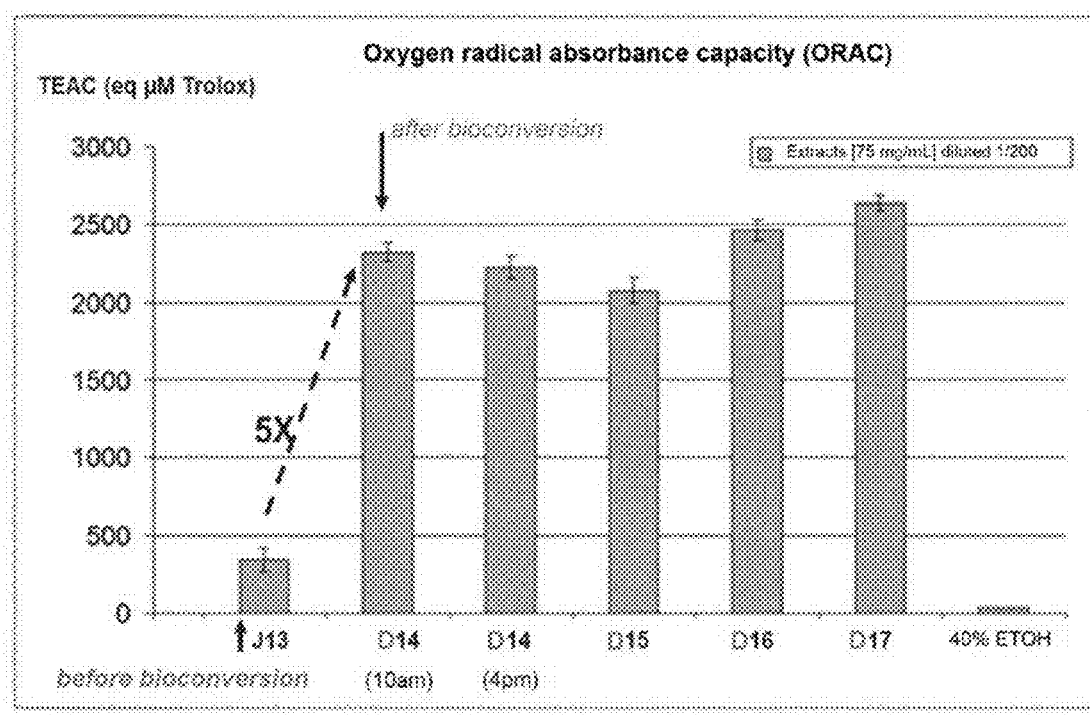

FIG. 4 shows the antioxidant activity of the extract containing 75 mg dry weight per ml, diluted to $1/200$th; before and after the bioconversion step.

Results:

On the x-axis, a PCC extract WO2 taken after X days of culture (time) D13, D14 at 10 am, D14 at 4 pm, and every 24 h after D15, D16, D17 and the activity of the last sample, the 40% ETOH blank control alone (no antioxidant activity).

It is seen that at D14, after 13 days of culture and 1 day after bioconversion (addition of AA), the TEAC (μM eq of TROLOX) quintupled to stabilize until D16-D17. In conclusion, bioconversion made it possible to potentiate the antioxidant activity by virtue of the presence of NPAs.

EXAMPLE 4: PHARMACOLOGY—ACTIVITY: IN VITRO MODEL OF INDUCED ATOPIC Dermatitis (AD)

Multiparametric evaluation of the anti-inflammatory activity of Mimosa pudica in an in vitro model exhibiting an atopic dermatitis phenotype. The pharmacological model was described by Castex-Rizzi et al. (Br J Dermatol. 2014. 170 Suppl 1:12-8)

4.1. Extracts and Compounds

PCC extracts collected from crushed, dried, standardized Mimosa pudica culture medium W01D15 (with bioconversion) were dissolved/diluted in solution in 40% EtOH at initial concentrations of 75 mg/ml. The compounds were solubilized extemporaneously for viability tests as well as at the appropriate dose in order to measure pharmacological action on the model of induced atopic dermatitis.

4.2 Cell Type

Normal human epidermal keratinocytes (NHEKs) from Lonza. The cells are amplified under standard culture conditions.

4.3 Induction of an Atopic Dermatitis Phenotype

NHEK cells are seeded and cultured in Keratinocyte-SFM culture medium. The culture medium is then replaced with medium containing the compounds and extracts to be tested or solvent used as control (EtOH40% in concentrations equivalent to those used during treatment with the compounds). After a "pre-incubation" of 1 h the inflammation inducer mixture (Poly (I:C), IL4, IL13) is added and the cells are cultured for 24 h.

A control without inducer and without compound is also carried out in parallel, allowing us to validate the induced model (NHEK vs NHEK+inducers).

NHEK cells are also treated with a reference product, 0.29 mM dexamethasone, and used as efficacy control.

RNA is extracted from the cells after 24 hours of incubation with the inducer mixture.

4.5 Analysis of Differential Expression by RT-qPCR 4.5.1. Extraction of Total RNAs and cDNA Synthesis Extraction was carried out using RNABle (Eurobio) and the RNeasy Mini Kit from QIAGEN. The total RNAs extracted are assayed on a spectrophotometer (NanoDrop, ND1000, Thermo Scientific) and their qualities analysed on agarose gel.

4.5.2. The Quantitative PCR Technique

Principle

Real-time PCR is a precise, sensitive and rapid method that allows the relative quantification of the rate of expression of a target gene relative to that of a ubiquitously expressed reference gene. This technique makes it possible to quantify messenger RNA. This operation is carried out after reverse transcription of the RNAs into complementary DNA by extension of two primers located on either side of the target to be amplified using a DNA polymerase. Incorporation of a fluorophore (SYBR Green) during the hybridization step of exponential amplification allows quantification and real-time monitoring of the amount of neo-formed amplification product. Quantitative values are obtained from the number of threshold cycles (Ct: for Cycle threshold) at which the signal increase, associated with exponential growth of the PCR product, begins to be detected using a Biosystems PE analysis program according to the manufacturer's manual. Thus, the greater the amount of cDNA of the target gene at time zero, the lower the Ct number (cycle number to reach the threshold).

In order to standardise the quantitative RT-PCR analyses, it is necessary to quantify in the same experiment at least one endogenous control called the "reference gene". This "reference gene" must have a constitutive expression independent of the treated or untreated condition of the cells. The relative expression of the selected target genes is calculated by the ΔΔCt method using the RQ (Relative Quantification) software provided by the manufacturer (Applied Biosystems). The expression values of each gene induced by a given compound are also normalized so that the value of the control NHEK cells (untreated cells and cells treated with DMSO in % identical to that used as carrier for the compound) is equal to 1. Therefore, the RQ value obtained for each compound for a given gene represents the relative expression of this gene after treatment in relation to the control cells whose expression is 1.

Choice of Primers

The primers were chosen with the assistance of computer programs including Oligo 4 (National Biosciences, Plymouth, Minn.). The selection criteria concern the size of the fragment to be amplified (between 80 and 120 nucleotides), the size of the primers (between 21 and 25 nucleotides), the hybridization temperature of the primers (about 65° C.) and the position of the primers; indeed, the primers are designed such that one of the 2 primers straddles an intron and an exon or that the 2 primers are in two different exons if the intron separating them is greater than 2 kbp. The choice of the quite specific position of the primers avoids the amplification of genomic DNA in case of sample contamination even if no contamination has been observed on the dissociation curves (ABI, 7900HT). All these precautions stem from the fact that the least contamination by genomic DNA can have a very significant impact on the results obtained by a technology as sensitive as quantitative RT-PCR. Another important selection criterion is to ensure that the selected primer pair does not form a duplex that would interfere non-specifically with the specific PCR product obtained and thus distort the result (inherent in the SYBR Green technique used). Finally, the primers are chosen so that they do not contain consensus regions and/or polymorphisms. The total specificity of the nucleotide sequences chosen as primers of the target gene is tested by preparing a collage (nucleotide-nucleotide blast) over the entire human genome (Altschul et al., J. Mol. Biol., 215:403-410, 1990).

Standard Amplification Curve

The efficiency of the primers was tested by 5-fold serial dilutions (4 points) prepared in duplicate on RNA extracted from the NHEK cells. Only primer pairs with an efficiency close to 100% (slope equal to 3.32) are retained. A no-template control (NTC) amplification is also performed to ensure that no duplexes are formed that could distort the quantitative PCR results obtained by the SYBR Green method. The dissociation curve obtained on the 7900HT device is used to ensure that the amplification product obtained is unique. A regular check of the standard amplification curve is carried out in order to prevent any decrease in primer efficiency.

Amplification

The amplifications are performed on an ABI Prism 7900 Sequence Detection System (Applied Biosystems) using the SYBR Green method (SYBR Green PCR Core Reagents Kit, Applied Biosystems). Amplification consists of a denaturation step (10 min at 95° C.) then by the repetition of 40 cycles of hybridization (15 sec at 95° C.) and extension (1 min at 65° C.) which ensure an exponential duplication of each strand.

Genes Quantified

The genes characteristic of an AD phenotype that were quantified are listed in the left column in Table 2. The response values are normalized. From left to right in the table, the column labelled AD indicates the level of induction of each gene (in the absence of active agent). The column labelled ETOH40 corresponds to the values generated by the solvent alone without active agent in order to detect possible response interference due to the solvent. The next 2 columns, labelled W01, are the test sample at two concentrations, 1.5 mg/ml and 0.75 mg/ml, respectively, after induction. The last column shows the values generated by the positive control, 0.28 mM dexamethasone.

Results

TABLE 2

| | | AD | EtOH40 | W01 (1.5 mg/ml) | W01 (0.75 mg/ml) | 0.28 mM DEXA |
|---|---|---|---|---|---|---|
| Anti-microbial peptide, innate immunity, receptor | | | | | | |
| DEFB103A | Defensin, beta 103B | 27.19 | 11.05 | 498.69 | 32.02 | 107.56 |
| RNASE7 | Ribonuclease, RNase A family, 7 | 31.69 | 27.32 | 117.21 | 13.69 | 43.23 |
| S100A7 | S100 calcium binding protein A7 | 75.22 | 79.10 | 102.11 | 98.50 | 79.12 |
| TLR3 | Toll-like receptor 3 | 15.17 | 15.03 | 0.30 | 0.75 | 2.79 |
| Interleukins | | | | | | |
| IFNB1 | Interferon, beta 1, fibroblast | 30.55 | 14.88 | 0.24 | 0.13 | 1.90 |
| IL1A | Interleukin 1, alpha | 56.38 | 41.86 | 19.39 | 7.55 | 8.54 |
| IL1B | Interleukin 1, beta | 67.18 | 33.58 | 4.77 | 3.52 | 2.63 |
| IL4R | Interleukin 4 receptor | 9.63 | 9.33 | 4.35 | 3.14 | 7.03 |
| TSLP | Thymic stromal lymphopoietin | 50.67 | 31.31 | 0.04 | 0.04 | 1.80 |
| Chemokines | | | | | | |
| CCL13 | Chemokine (C-C motif) ligand 13 | 3.31 | 2.01 | 0.90 | 0.41 | 1.98 |
| CCL11 | Chemokine (C-C motif) ligand 11 | 0.97 | 0.93 | 0.56 | 0.12 | 1.14 |
| CCL20 | Chemokine (C-C motif) ligand 20 | 85.57 | 55.47 | 0.60 | 0.19 | 28.94 |
| CCL27 | Chemokine (C-C motif) ligand 27 | 16.82 | 12.08 | 0.77 | 2.34 | 0.71 |
| CCL5 | Chemokine (C-C motif) ligand 5 | 78.90 | 99.37 | 2.15 | 2.58 | 49.90 |
| IL15 | Interleukin 15 | 31.54 | 34.53 | 1.44 | 1.50 | 29.16 |
| IL8 | Interleukin 8 | 133.07 | 78.39 | 0.23 | 0.11 | 7.89 |
| CX3CL1 | Fractalkine | 62.38 | 119.24 | 5.90 | 1.83 | 36.63 |

The results presented in the tables show the inhibitory power of the pro-inflammatory and inflammatory genes (interleukins and chemokines) and also the induction of antimicrobial peptides (which are deficient in atopic dermatitis). The antimicrobial peptides that are strongly induced are: DEFB103, RNASE7, and notably psoriasin (S100A7) by W01 in a dose-dependent manner. The inhibited interleukins are: IFNB1, IL1A and IL1B. IL4R and TLR3 receptors are suppressed, the latter correlates well with the near-complete inhibition of the chemokine TSLP. These 2 factors are overexpressed in AD patients and more particularly in the case when pruritis appears (Miyagaki et al. 2015. J Dermatol Science 78:89-94). This is the first time that we have demonstrated such a strong anti-TSLP inhibition by the *Mimosa pudica* PCC extract in this in vitro model of AD. The chemokines CCL11, CCL13, CCL20, CCL27, CCLS, CX3CL1, IL15 and notably IL8 were strongly inhibited by extract W01 regardless of the dose. In summary, this experiment shows that the *Mimosa pudica* PCC extract inhibits the majority of pro-inflammatory and inflammatory factors as well as, if not better than, the dexamethasone control, in particular the factor TSLP which causes pruritus in patients with AD.

The invention claimed is:

1. A process for in vitro preparation of a *Mimosa pudica* cell extract having a mimosine content of less than 5 ng/g dry weight, comprising the following steps:
   a. providing sterile plant material of *Mimosa pudica*,
   b. dedifferentiating cells from the plant material,
   c. forming a suspension culture of the undifferentiated cells in a liquid medium for maintaining said cells in the undifferentiated state,
   d. propagating an undifferentiated cell biomass in the culture medium,
   e. stopping the propagation and obtaining a cell extract having a mimosine content of less than 5 ng/g dry weight;
   wherein the culture medium of step c) and/or step d) contains a phenyl-ammonia-lyase substrate.

2. The process according to claim 1, wherein the *Mimosa pudica* plant material is selected from the group consisting of leaf, stem, petiole, root, seed, flower and bud.

3. The process according to claim 1, wherein step b) is carried out on a solid medium containing one or more growth factors.

4. The process according to claim 1, wherein step b) is repeated so as to obtain calluses of dedifferentiated cells.

5. The process according to claim 1, wherein step c) is carried out in a liquid medium containing one or more growth factors.

6. The process according to claim 5, wherein the one or more growth factors are the same as that or those of the dedifferentiation medium.

7. The process according to claim 1, further comprising the following additional steps:
   f. liquid/solid separation,
   g. recovering a cell extract consisting of biomass separated from the culture medium having a mimosine content of less than 5 ng/g dry weight.

8. The process according to claim 1, further comprising an additional step of crushing the extract and recovering a crushed cell material having a mimosine content of less than 5 ng/g dry weight.

9. The process according to claim 1, wherein the resulting extract contains at least one N-phenylpropenoyl amino acid.

10. The process according to claim 9, wherein the N-phenylpropenoyl amino acid is selected from the group consisting of:

P1: 1-O-(4-coumaroyl)-β-D-glucose $C_{15}H_{18}O_8$

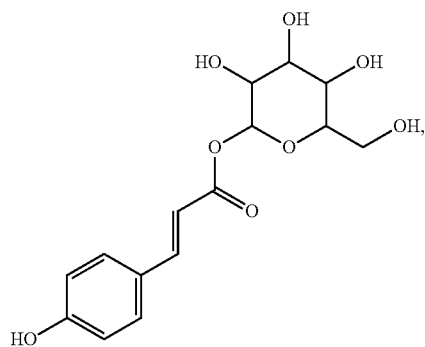 [SMILES: O=C(/C=C/c1ccc(O)cc1)OC1OC(CO)C(O)C(O)C1O]

P2: N-p-Coumaroylaspartic acid or Aspartic acid; (S)-form, N-(4-Hydroxycinnamoyl $C_{13}H_{13}NO_6$

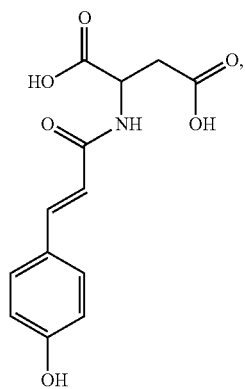 [SMILES: O=C(O)CC(NC(=O)/C=C/c1ccc(O)cc1)C(=O)O]

P3: N-cis-(p-Coumaroyl)glutamic acid or Glutamic acid; (S)-form, N-(4-Hydroxy-Z-cinnamoyl)

$C_{14}H_{16}NO_6$

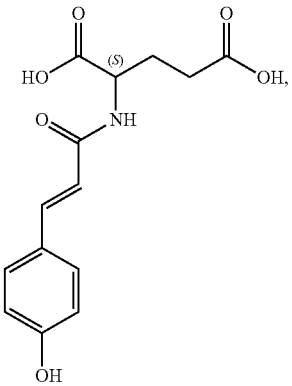

P5: 4-hydroxycinnamide $C_9H_9NO_2$

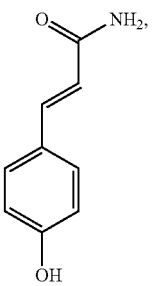 [SMILES: NC(=O)/C=C/c1ccc(O)cc1]

P6: Glutamic acid; (S)-form, N-cinnamoyl $C_{14}H_{14}NO_5$

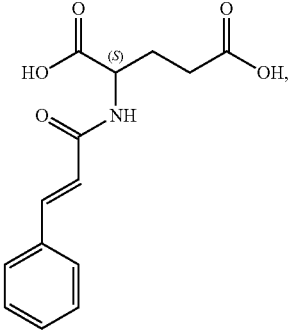

mixtures thereof.

* * * * *